United States Patent

Waki et al.

[11] Patent Number: 6,031,017
[45] Date of Patent: Feb. 29, 2000

[54] PHOTOCURED CROSS-LINKED-HYALURONIC ACID GEL AND METHOD OF PREPARATION THEREOF

[75] Inventors: Michinori Waki; Kenji Miyamoto, both of Tokyo, Japan

[73] Assignee: Seikagaku Corporation, Tokyo, Japan

[21] Appl. No.: 09/068,227

[22] PCT Filed: Nov. 14, 1996

[86] PCT No.: PCT/JP96/03349

§ 371 Date: May 5, 1998

§ 102(e) Date: May 5, 1998

[87] PCT Pub. No.: WO97/18244

PCT Pub. Date: May 22, 1997

[30] Foreign Application Priority Data

Nov. 15, 1995 [JP] Japan ................................. 7-319825

[51] Int. Cl.[7] .................................................. C08L 5/08
[52] U.S. Cl. ............................. 522/84; 522/89; 522/86; 522/87; 522/88
[58] Field of Search ................................ 522/87, 88, 89, 522/86, 84

[56] References Cited

U.S. PATENT DOCUMENTS 5,410,016  4/1995  Hubbell et al. ........................ 528/354
5,462,976  10/1995 Matsuda et al. ......................... 522/74
5,700,848  12/1997 Soon-Shiong et al. .................... 522/7

FOREIGN PATENT DOCUMENTS 0 554 898    8/1993  European Pat. Off. ........ C08B 37/10
0 554 898 A2 11/1993  European Pat. Off. .

OTHER PUBLICATIONS

Asaio Journal, vol. 39, No. 3, 1993, pp. M327–M331, XP000616745 Takehisa Matsuda et al.: "Newly designed tissue adhesion prevention technology based on photocurable mucopolysaccharides".

*Primary Examiner*—James J. Seidleck
*Assistant Examiner*—Sanza L. McClendon
*Attorney, Agent, or Firm*—Sughrue, Mion, Zinn, Macpeak & Seas, PLLC

[57] ABSTRACT

A photocured crosslinked-hyaluronic acid gel, which has a storage modulus (G') of from 50 to 1500 Pa, a loss modulus (G") of from 10 to 300 Pa, and a tangent delta (G"/G') of from 0.1 to 0.8 in dynamic viscoelasticity at a frequency of 10 Hz, and which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups, methods for preparing the same, and uses thereof as biomedical materials.

19 Claims, 2 Drawing Sheets

PHOTOCURED CROSS-LINKED-HYALURONIC ACID GEL AND METHOD OF PREPARATION THEREOF

TECHNICAL FIELD

The present invention relates to a biocompatible photocured crosslinked-hyaluronic acid gel that is a hydrogel having specific physical properties, methods for preparing the same, and uses thereof as biomedical materials.

BACKGROUND ART

Hyaluronic acid exists in animal tissues and has biocompatibility and biodegradability. With regard to physical properties, it has superior properties such as a highly water-absorbing property, and the aqueous solution thereof has high viscosity.

A hydrogel is obtained by chemically modifying hyaluronic acid, crosslinking the modified hyaluronic acid by some methods to form a network structure, and incorporating an aqueous medium such as water into the network structure. The hydrogel shows viscoelasticity as well as viscosity.

The crosslinked hyaluronic acid apparently forms macromolecules irrespective of the bonding mode. The biodegradability of the crosslinked hyaluronic acid can be controlled by adjusting the degree of crosslinking.

There are various crosslinking modes. For example, as a crosslinking mode making use of a hydrophobic bonding or an ionic bonding, a crosslinking of hyaluronic acid by introducing a nucleophilic reagent thereto (JP-W-3-502704 (corresponding to U.S. Pat. No. 4,937,270), the term "JP-W" as used herein means an "unexamined published international patent application"), a crosslinking via a hydrophobic bonding by esterification of hyaluronic acid (U.S. Pat. No. 4,851,521), and a crosslinking via an ionic bonding by polyvalent ions (EP 0507604 A2) have been known. Since they are crosslinked by a weak bonding force compared to that of a covalent bonding, they are susceptible to influences of external changes such as pH, ionic strength, temperature and the like. In addition, when they are used as biomedical materials, remainability in a living body is short, and it is difficult to control properly remainability in the body so as to maintain the physiological effects of hyaluronic acid for the body.

Furthermore, as a crosslinking mode of binding of hyaluronic acid molecules by a covalent bonding, a crosslinking via divinylsulfone (JP-B-4-30691 (corresponding to U.S. Pat. No. 4,582,865), the term "JP-B" as used herein means an "examined Japanese patent publication") and a crosslinking via an epoxide (JP-W-61-502729 (corresponding to U.S. Pat. No. 4,886,787), JP-A-5-140201, the term "JP-A" as used herein means an "unexamined published Japanese patent application") have been known. However, the crosslinking agents or the crosslinking compounds used in these crosslinkings are toxic. Besides, a three-dimensional network structure is constituted by crosslinking at the same time when divinylsulfone, epoxide or the like is introduced into hyaluronic acid, and the formed crosslinked hyaluronic acid gel is insolubilized in a solvent such as water and the like. Unreacted low-molecular compounds thus incorporated into the network structure are difficult to separate and remove.

On the other hand, a crosslinking of hyaluronic acid by a photocured crosslinking reaction through irradiation with ultraviolet rays (JP-A-6-73102 (corresponding to U.S. Pat. No. 5,462,976), *ASAIO Journal,* 38, M154-M157 (1992)) has also been known. This crosslinking mode has the advantages that a photoreactive hyaluronic acid derivative into which a photoreactive crosslinking group is introduced is water-soluble before photocured crosslinking and a three-dimensional network structure is not formed at the time so that unreacted low-molecular compounds can be removed with ease; the photoreaction itself is such a clean reaction that yields a photocured crosslinked-hyaluronic acid derivative free from unreacted low-molecular compounds; and the resulting crosslinked structure is formed by a covalent bonding so that the control of the remainability of the photocured crosslinked-hyaluronic acid derivative can be easily performed by controlling a degree of crosslinking.

Also, when the above-described photocured crosslinked-hyaluronic acid derivative was intended to apply for uses as biomedical materials, e.g., antiadhesive materials, those in the film-like form had been investigated (*ASAIO Journal,* 38, M154-M157 (1992)), but it has been difficult to prevent adhesions in fine parts of tissues or organs. Thus, an injectable photocured crosslinked-hyaluronic acid gel which can be injected into such a fine site has therefore been demanded.

However, hydrogel of a photocured crosslinked-hyaluronic acid and methods for preparing the same as disclosed in the present invention have been unknown.

A conventional crosslinked hyaluronic acid hydrogel has difficulty in removing impurity such as unreacted low-molecular compounds and the like and controlling the physical properties of the hydrogel. Furthermore, it has been difficult to establish conditions for preparing hydrogel having desired physical properties.

DISCLOSURE OF THE INVENTION

First object of the present invention is to provide a photocured crosslinked-hyaluronic acid gel containing an aqueous medium which is obtained by irradiation with ultraviolet rays of a photoreactive hyaluronic acid derivative into which the photoreactive crosslinking group is introduced and dimerization of the mutual photoreactive crosslinking groups to form a cyclobutane ring and to thereby form a network structure, and methods for easily preparing the above-described gel.

Second object of the present invention is to provide an injectable biomedical material comprising a photocured crosslinked-hyaluronic acid gel which is excellent in safety, biocompatibility and biodegradability.

As a result of intensive studies, the inventors of the present invention have succeeded in achieving the above objects by the following construction:

1) A photocured crosslinked-hyaluronic acid gel, which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions, method of measurement:
   oscillation test method, stress control
   measuring temperature: 37° C.
   measuring geometry: 4 cm
   gap: 800 μm
   frequency: 10 Hz, and
   which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups;

2) A photocured crosslinked-hyaluronic acid gel,
which has a crosslinking extent of from 0.01 to 0.5% per mole of a constituent disaccharide unit of the hyaluronic acid, and
which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups;

3) A photocured crosslinked-hyaluronic acid gel,
which has a water absorption of 2,000 to 15,000% as defined as follows:

water absorption (%)=weight of absorbed water /weight of dried gel×100, and which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups;

4) The photocured crosslinked-hyaluronic acid gel according to any one of 1) to 3) above,
wherein said photoreactive crosslinking group is a cinnamic acid derivative containing a spacer and chemically links to a functional group of hyaluronic acid to afford said photoreactive hyaluronic acid derivative;
said mutual photoreactive crosslinking groups of said photoreactive hyaluronic acid derivative are dimerized by irradiation with ultraviolet rays to form a cyclobutane ring and to thereby form a network structure; and
said gel is a hydrogel containing an aqueous medium in said network structure;

5) The photocured crosslinked-hyaluronic acid gel according to 4) above, wherein said spacer is a group derived from an amino alcohol, an amino acid or a peptide;

6) The photocured crosslinked-hyaluronic acid gel according to 4) or 5) above, wherein said photoreactive crosslinking group is represented by the following formula (1) or (2):

$$—NH(CR^1R^2)_nOCOCH\!=\!CH—Ph \quad (1)$$

wherein $R^1$ and $R^2$ each independently represents a hydrogen atom or an alkyl group having from 1 to 8 carbon atoms; Ph represents a phenyl group; and n represents an integer of from 2 to 18;

$$—A—NH—Ph—CH\!=\!CHCOOR^3 \quad (2)$$

wherein $R^3$ represents an alkyl group having from 1 to 8 carbon atoms or an aralkyl group; A represents —(NHCR$^4$R$^5$CO)$_m$— or —NH(CR$^4$R$^5$)$_h$CO—; $R^4$ and $R^5$ each independently represents a hydrogen atom or an alkyl group having from 1 to 8 carbon atoms; —Ph— represents a para-phenylene group; m represents an integer of from 1 to 6; and h represents an integer of from 1 to 18;

7) The photocured crosslinked-hyaluronic acid gel according to any one of 1) to 6) above, wherein said photoreactive crosslinking group is introduced in a proportion of from 0.05 to 10% per mole of a constituent disaccharide unit;

8) A photocured crosslinked-hyaluronic acid gel,
which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups and then by a heat treatment of the crosslinked product;

9) A photocured crosslinked-hyaluronic acid gel,
which has a storage modulus (G') of from 50 to 1500 Pa, a loss modulus (G") of from 10 to 300 Pa, and a tangent delta (G"/G') of from 0.1to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a hydrogel obtained by a heat treatment of a photoreactive hyaluronic acid derivative in which a photoreactive crosslinking group is chemically linked to a functional group of the hyaluronic acid, and then by irradiation with ultraviolet rays of the heated photoreactive hyaluronic acid derivative and crosslinking of mutual photoreactive crosslinking groups;

10) A photocured crosslinked-hyaluronic acid gel,
which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a-hydrogel obtained by a heat treatment of a photoreactive hyaluronic acid derivative in which a photoreactive crosslinking group is chemically linked to a functional group of the hyaluronic acid, and then by irradiation with ultraviolet rays of the heated photoreactive hyaluronic acid derivative and crosslinking of mutual photoreactive crosslinking groups, and then by a heat treatment of the crosslinked product again;

11) The photocured crosslinked-hyaluronic acid gel according to any one of 1) to 10) above, wherein the endotoxin content of the gel is 0.25 endotoxin unit (EU)/g or less;

12) A method for preparing a photocured crosslinked-hyaluronic acid gel comprising:
irradiating with ultraviolet rays an aqueous medium solution containing from 0.5 to 10% by weight photoreactive hyaluronic acid derivative in which a photoreactive crosslinking group is chemically linked to a functional group of the hyaluronic acid; and forming an intermolecular and/or intramolecular crosslinking by dimerization of the mutual photoreactive crosslinking groups to provide a network structure.

13) The method for preparing a photocured crosslinked-hyaluronic acid gel according to 12) above, wherein a heat treatment is conducted before and/or after irradiation with ultraviolet rays of said aqueous medium solution of the photoreactive hyaluronic acid derivative;

14) The method for preparing a photocured crosslinked-hyaluronic acid gel according to 13) above, wherein said heat treatment is conducted at from 100 to 125° C. for from 5 to 30 minutes with high pressure steam;

15) A biomedical material comprising the photocured crosslinked-hyaluronic acid gel according to any one of 1) to 11) above;

16) The biomedical material according to 15) above, which has an antiadhesive effect;

17) A biomedical material kit comprising a crosslinked hyaluronic acid gel and a container containing said gel in such a state that it can be taken out;

18) The biomedical material kit according to 17) above, wherein said container is a container which can push out said gel for injection;

19) A biomedical material kit comprising the photocured crosslinked hyaluronic acid gel as described in any one of 1) to 11) and a container containing said gel in such a state that it can be taken out; and 20) The biomedical material kit according to 19) above, wherein said container is a container which can push out said gel for injection.

BEST MODE FOR PRACTICING INVENTION

The present invention will be explained in detail below.

The term "photocured crosslinked-hyaluronic acid derivative" as used in the present invention is intended to include a derivative, as a concept, obtained by irradiation with ultraviolet rays of a photoreactive hyaluronic acid derivative in which a photoreactive crosslinking group is chemically linked and dimerization of the mutual photoreactive crosslinking groups to crosslink the hyaluronic acid derivative and to thereby form a network structure. The term "photocured crosslinked-hyaluronic acid gel" as used in the present invention means hydrogels, as a concept, containing an aqueous medium such as water, a buffer, physiological saline, buffered physiological saline, an aqueous solution containing a water-soluble organic solvent and the like as a dispersion medium in the network structure (three-dimensional network structure) of a photocured crosslinked-hyaluronic acid (hereinafter sometimes simply referred to as the "gel of the present invention"). The term "functional group of hyaluronic acid" as used in the present invention is intended to include functional groups which exist in hyaluronic acid and are capable of chemically linking to the photoreactive crosslinking groups. Representative examples of the functional groups are a carboxyl group and a hydroxyl group. The term "lower alkyl" or "lower alkoxyl" as used in the present invention is intended to include an alkyl group or an alkoxyl group which has from 1 to 8 carbon atoms, preferably from 1 to 4 carbon atoms.

In the gel of the present invention, at first the physical properties thereof is specified from the standpoint of viscoelasticity and at second the crosslinking structure thereof is specified from the standpoint of crosslinking extent.

The photoreactive crosslinking group in the photoreactive hyaluronic acid derivative of the present invention is not particularly limited as long as said group has a vinylene group which is capable of being dimerized by ultraviolet ray irradiation to form a cyclobutane ring and said group is derived from cinnamic acid or substituted derivatives thereof (for example, cinnamic acid derivatives and the like in which one or two hydrogen atoms at any positions of the benzene ring of cinnamic acid are substituted with a lower alkyl group (e.g., methyl, ethyl, propyl, isopropyl, butyl, t-butyl and the like), a lower alkoxyl group (e.g., methoxy, ethoxy, propoxy, isopropoxy, butoxy and the like), an amino group, a hydroxyl group and the like), a carboxy-lower-alkylthymine (e.g., 1-(2-carboxyethyl)thymine and the like), a carboxy-lower-alkyl-substituted coumarin (e.g., 7-coumaryloxyacetic acid and the like) and the like. Among them, a photoreactive crosslinking group into which a group derived from cinnamic acid or a derivative thereof is introduced is particularly preferred. Furthermore, as a photoreactive crosslinking group, a group derived from a compound in which a spacer is bound to a photoreactive compound such as cinnamic acid and the like is also preferred. Preferred spacers include those having two or more functional groups capable of binding to both of the functional group of a photoreactive compound such as cinnamic acid and the like and the functional group of hyaluronic acid. Concretely, amino acids or derivatives thereof, peptides, and amino alcohols and the like are preferred, and particularly amino alcohols are most preferred. The photoreactive crosslinking group may be introduced to any functional group of the constituent saccharide moieties of hyaluronic acid, i.e., N-acetyl-D-glucosamine and D-glucuronic acid, but it is particularly preferable to introduce said crosslinking group to the carboxyl group of the D-glucuronic acid.

In using cinnamic acid as a photoreactive crosslinking group and amino alcohol as a spacer, for instance, the photoreactive hyaluronic acid derivative with such structure is preferred that the carboxyl group of cinnamic acid is chemically linked to the hydroxyl group of the amino alcohol by an ester bond, and the amino group of the amino alcohol is chemically linked to the carboxyl group of hyaluronic acid by an amide bond. In using amminocinnamic acid as a photoreactive crosslinking group and an amino acid or a peptide as a spacer, the photoreactive hyaluronic acid with such structure is preferred that the carboxyl group of the spacer is chemically linked to the amino group of amino-cinnamic acid by an amide bond, and the amino group of said amino acid or peptide is chemically linked to the carboxyl group of hyaluronic acid by an amide bond.

Concretely, of the photoreactive crosslinking groups to which a spacer is bound, those represented by formula (1) or (2) shown below are particularly preferred.

$$—NH(CR^1R^2)_nOCOCH=CH—Ph \quad (1)$$

In formula (1), $R^1$ and $R^2$ each independently represents a hydrogen atom or a lower alkyl group (preferably having from 1 to 4 carbon atoms); Ph represents a phenyl group which may be not only a group expressed as $C_6H_5$— but also a group including a substituted benzene ring at any positions whose one or two hydrogen atoms are substituted with one or two substituents selected from a lower alkyl or alkoxyl group having from 1 to 4 carbon atoms, an amino group, a hydroxyl group and the like; and n represents an integer of from 2 to 18, preferably from 2 to 12.

The photoreactive crosslinking group represented by formula (1) is chemically linked to, e.g., the carboxyl group of hyaluronic acid by an amide bond to form a photoreactive hyaluronic acid derivative.

$$-A-NH-Ph-CH=CHCOOR^3 \quad (2)$$

In formula (2), $R^3$ represents a lower alkyl group, preferably an alkyl group having from 1 to 4 carbon atoms (e.g., methyl, ethyl or the like), or an aralkyl group having from 7 to 20 carbon atoms, preferably benzyl or phenethyl; A represents $-(NHCR^4R^5CO)_m-$ or $-NH(CR^4R^5)_nCO-$; $R^4$ and $R^5$ each independently represents a hydrogen atom or a lower alkyl group (preferably having from 1 to 4 carbon atoms); —Ph— represents a para-phenylene group which may be not only a group expressed as $-C_6H_4-$ but also a group including a substituted benzene ring whose hydrogen atom at the ortho or meta position in the benzene ring is substituted with a lower alkyl or alkoxyl group having from 1 to 4 carbon atoms, an amino group, a hydroxyl group or the like; m represents an integer of from 1 to 6, preferably from 1 to 3; and h represents an integer of from 1 to 18, preferably from 1 to 12.

The hyaluronic acid for use in the present invention is not particularly limited; however, a hyaluronic acid having a weight average molecular weight of from 10,000 to 5,000,000 is usually used as a starting material. Various molecular weights may be selected according to the use purpose. The weight average molecular weight is preferably from 500,000 to 3,000,000, and more preferably from 800,000 to 2,500,000. A water-soluble salt of hyaluronic acid such as an alkali metal salt (e.g., sodium salt, potassium salt or the like), an alkaline earth metal salt (e.g., calcium salt or the like) or the like is preferably used in the following synthetic method, but other salts or a free acid can also be used as far as they are soluble in the reaction solvent used and do not interfere with the reaction. The term "hyaluronic acid" as used hereinafter sometimes includes salts thereof.

The photoreactive hyaluronic acid derivative for use in the present invention can be prepared by dissolving hyaluronic acid in, for example, water alone or an aqueous solution containing a water-miscible organic solvent (for example, dioxane, dimethylformamide, N-methylpyrrolidone, acetamide, alcohol (e.g., methanol, ethanol), pyridine and the like) and introducing a photoreactive crosslinking group by, for example, a carbodiimide method in the presence of a water-soluble carbodiimide (e.g., 1-ethyl-3-(3-dimethylaminopropyl)-carbodiimide hydrochloride (hereinafter abbreviated as "EDC-HCl"), 1-ethyl-3-(3-dimethylaminopropyl)carbodiimide methiodide, 1-cyclohexyl-3-(2-morpholinoethyl)carbodiimide hydrochloride) and a condensation auxiliary agent (e.g., N-hydroxysuccinimide, N-hydroxybenzotriazole and the like).

Purification of the product obtained after the reaction can be carried out in a usual manner, for example, ethanol precipitation or dialysis. After purification and drying, the degree of substitution (hereinafter abbreviated as "DS", which is the ratio of introduction of the photoreactive crosslinking group per constituent disaccharide unit of hyaluronic acid) of the resulting photoreactive hyaluronic acid derivative can be obtained by measurement of the absorbance at around 269 nm of the product with a spectrophotometer.

Sterile and substantially endotoxin-free (e.g., endotoxin content of 0.25 EU/g or less) photoreactive hyaluronic acid derivatives and photocured crosslinked-hyaluronic acid gels can be obtained by using sterile or substantially endotoxin-free reagents, water, containers and the like and paying attention to sterilization of the working environment in the preparation.

Specific compounds used for introduction of a photoreactive crosslinking group to hyaluronic acid include that represented by the following formula (1-1) or (2-1):

$$H_2N(CR^1R^2)_nOCOCH=CH-Ph \quad (1\text{-}1)$$

wherein $R^1$, $R^2$, Ph, and n are as defined above.

$$H-A-NH-Ph-CH=CHCOOR^3 \quad (2\text{-}1)$$

wherein A, —Ph—, and $R^3$ are as defined above.

Compounds (1-1) and (2-1) are preferably used in the form of a salt, for example, an acid addition salt such as a hydrochloride, a hydrobromide, a hydrofluoride or the like, a hydrochloride being particularly preferred.

Concretely, hydrochloride (1-2) of compound (1-1) can be synthesized according to the following reaction scheme:

First Reaction $$R^6HN(CR^1R^2)_nOH(3)+XCOCH=CH-Ph(4) \rightarrow R^6HN(CR^1R^2)_nOCOCH=CH-Ph(5)$$

Second Reaction $$(5)+HCl \rightarrow HCl.H_2N(CR^1R^2)_nOCOCH=CH-Ph \quad (1\text{-}2)$$

wherein $R^6$ represents an amino-protecting group which can be cleaved with acid, e.g., a t-butoxycarbonyl group and the like; and X represents a halogen atom, e.g., a chlorine atom and the like.

Herein, specifically, compound (1-2) is synthesized as follows.

An organic solvent (e.g., chloroform and the like) is added to compound (3), and an organic base (e.g., triethylamine and the like) is added thereto under cooling with ice. Compound (4) and a basic catalyst (e.g., 4-dimethylaminopyridine and the like) are added thereto successively. After stirring the mixture at room temperature, an organic solvent (e.g., ethyl acetate and the like) is added to the reaction mixture, and the mixture is washed successively with several portions of a weak acid aqueous solution, water, several portions of a weak alkali aqueous solution, water, a saturated sodium chloride aqueous solution and the like. The organic solvent layer separated is dried over anhydrous sodium sulfate or the like. The desiccant and the like are removed by filtration, and the filtrate is dried under reduced pressure to give compound (5).

A 1 to 5 M solution of-hydrogen chloride in an organic solvent (e.g., dioxane and the like) is added to compound (5) under cooling with ice, followed by stirring. An organic solvent (e.g., diethyl ether and the like) is added thereto, and the crystals precipitated are collected by filtration. The crystals are washed with an organic solvent and dried under reduced pressure to give compound (1-2).

Concretely, hydrochloride (2-2) of compound (2-1) can be synthesized according to the following reaction scheme:
First Reaction $$R^6-A-OH(6)+H_2N-Ph-CH=CHCOOR^3(7) \rightarrow R^6-A-HN-Ph-CH=CHCOOR^3(8)$$

Second Reaction $$(8)+HCl \rightarrow HCl.H-A-HN-Ph-CH=CHCOOR^3 \quad (2\text{-}2)$$

wherein $R^3$ and $R^6$ are as defined above.

Furthermore, compound (2-2) is specifically synthesized as follows.

An organic solvent (e.g., chloroform and the like) is added to compound (6), and an activator (e.g., dimethylphosphinothioyl chloride and the like) is added thereto in the presence of an organic base (e.g., triethylamine and the like) while cooling with ice, thereby to activate the carboxyl group of compound (6). After activation of compound (6), compound (7) is added thereto in the presence of an organic base (e.g., triethylamine and the like) while ice-cooling, followed by stirring at room temperature. An organic solvent (e.g., ethyl acetate and the like) is added to the reaction mixture, and the mixture is washed successively with several portions of a weak acid aqueous solution, water, several portions of a weak alkali aqueous solution, water, a saturated sodium chloride aqueous solution and the like. The organic solvent layer separated is dried over anhydrous sodium sulfate or the like. The desiccant and the like are removed by filtration, and the filtrate is dried under reduced pressure to give compound (8).

A 1 to 5 M solution of hydrogen chloride in an organic solvent (e.g., dioxane and the like) is added to compound (8) under cooling with ice, followed by stirring. An organic solvent (e.g., diethyl ether and the like) is added thereto, and the crystals precipitated are collected by filtration, washed with an organic solvent, and dried under reduced pressure to give compound (2-2).

The existence of a spacer incorporated into the photoreactive crosslinking group greatly contributes to an improvement in photoreactivity of the photoreactive hyaluronic acid derivative, while the improvement depends on the degree of freedom and hydrophobic bonding properties of the spacer. The improved sensitivity in photoreactivity brought about by the spacer makes it possible to achieve photocured crosslinking at such a low introduction ratio of the photoreactive crosslinking group while photocured crosslinking has heretofore been difficult under such conditions.

According to a conventional technique, when the above-described photoreactive hyaluronic acid derivative is crosslinked by light irradiation, an aqueous solution of a photoreactive hyaluronic acid derivative is first dried over a container and the like into a film or the like, and then irradiated with ultraviolet rays to obtain a photocured crosslinked-hyaluronic acid film. Not only does a film transmit ultraviolet rays easily, but also the photoreactive crosslinking groups are oriented to get closer to each other because of their hydrophobic nature while the film is being dehydrated or water is evaporating during the film formation. It has been accepted that thus formed situation serves in favor of photoreaction. For instance, in case that a photoreactive crosslinking group is a cinnamic acid residue, when the distance between the mutual cinnamic acid residues is 4 Å, the molecules can be dimerized, i.e., crosslinked, by irradiation with ultraviolet rays of specific wavelength, but not at other intermolecular distance. Therefore, film formation that makes photoreactive crosslinking groups closer to each other has been considered as an important step for achieving photoreaction. Further, trans-cinnamic acid can be dimerized by irradiation with ultraviolet rays under the above-described conditions, while its geometrical isomer (i.e., cis-cinnamic acid) is inactive to dimerization. When an aqueous solution of a conventional photoreactive hyaluronic acid derivative is irradiated with ultraviolet rays, it has been considered that crosslinking may be difficult because water molecules seem to prevent the mutual photoreactive crosslinking groups from getting closer and trans-to-cis isomerization takes place predominantly over dimerization.

The inventors of the present invention found that a photocured crosslinked-hyaluronic acid gel can be formed by preparing an aqueous solution of a photoreactive hyaluronic acid derivative in a high concentration to make the mutual photoreactive crosslinking groups closer more frequently, making the solution layer into a shape allowing ultraviolet rays transmittable with ease, followed by irradiation thereto with ultraviolet rays.

According to the present invention, when the photoreactive hyaluronic acid is irradiated with ultraviolet rays, photocured crosslinked-hyaluronic acid gel having desired physical properties such as viscoelasticity and the like can be obtained by properly selecting photoreaction conditions such as the concentration of the photoreaction solution, irradiation time of the ultraviolet rays and the like, or DS.

A preferred concentration of the photoreactive hyaluronic acid derivative solution in an aqueous medium which is to be irradiated with light (hereinafter sometimes referred to as a "photoreaction concentration") is about from 0.5 to 10% by weight. In using a photoreactive hyaluronic acid derivative having a molecular weight of about 1,000,000, a concentration of from 1 to 4% by weight is more preferred. At lower concentrations, isomerization takes place in preference to dimerization as hereinafter mentioned. On the contrary, at higher concentrations, it is difficult to obtain uniform gel.

Figure 1:
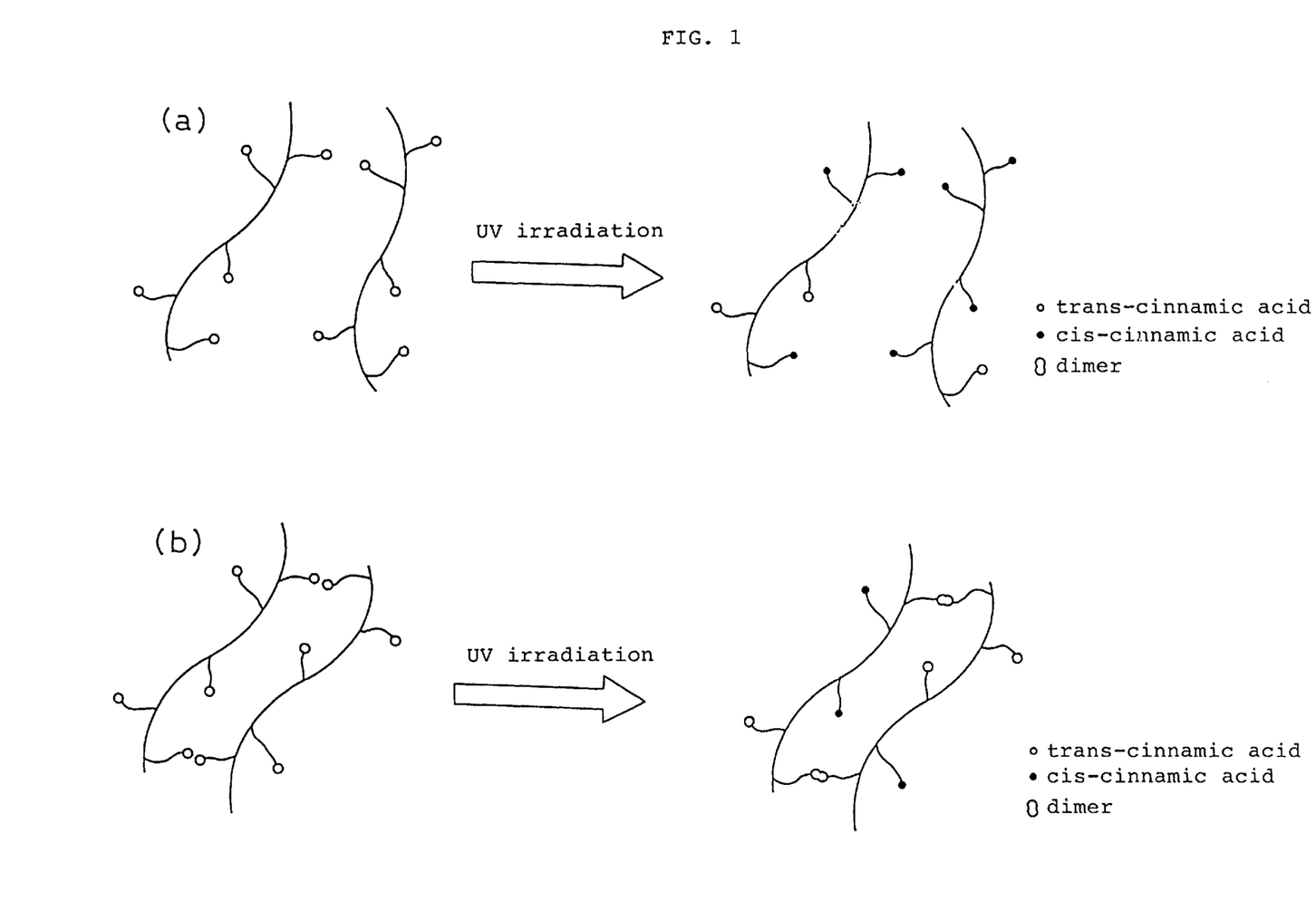
FIG. 1 is a drawing showing a concept of photocured crosslinking in a photoreactive hyaluronic acid derivative solution.

When a more diluted aqueous solution in concentration than said concentration specified is irradiated with ultraviolet rays, isomers tend to be produced preferentially as described above. On continuing irradiation with ultraviolet rays, the saccharide chain itself of hyaluronic acid will be cleaved by the influence of ultraviolet rays, resulting in reduction of molecular weight. From these standpoints, it is of importance to create a reaction situation in which photocured crosslinking reaction proceeds efficiently without adverse influences on the saccharide chain of hyaluronic acid. It is essential therefore to prepare an aqueous solution at concentrations specified above. FIG. 1 shows the concept drawing of photocured crosslinking in an aqueous medium, in which (a) shows the change of a photoreactive hyaluronic acid derivative in a diluted solution on irradiation with ultraviolet rays. Water molecules prevent the mutual photoreactive crosslinking groups from taking a molecular arrangement ready for crosslinking, and isomerization predominates as a result. In (b) the change of a photoreactive hyaluronic acid derivative in a solution at a specified concentration on irradiation with ultraviolet rays is shown. The hydrophobic photoreactive crosslinking groups, being less subject to the interference of water molecules than in a diluted solution, seem to attract each other by the hydrophobic bonding force to take a molecular arrangement ready for crosslinking. Thus, the photoreactive crosslinking groups are dimerized by the irradiation while including the aqueous medium, thereby accomplishing crosslinking. In order to secure improved photoreactivity in crosslinking in the solution at the specified concentration, it is particularly preferable to use a photoreactive hyaluronic acid derivative incorporated with a photoreactive crosslinking group containing the above-described spacer and having high flexibility.

The photoreaction concentration mentioned above is dependent on the degree of substitution (DS) of the photoreactive crosslinking group incorporated into hyaluronic acid. DS can be calculated based on the ratio (%) of introduction of the photoreactive crosslinking group per constituent disaccharide unit of hyaluronic acid. For example, DS of a photoreactive hyaluronic acid derivative having one photoreactive crosslinking group per constituent disaccharide unit or per constituent 200 saccharide units is 100% or 1%, respectively. Under the same irradiation conditions with light, the lower the DS is, the lower the ratio of crosslinking is.

In the present invention, DS of the photoreactive hyaluronic acid derivative for achieving crosslinking at the specified photoreaction concentration mentioned above may be about from 0.05 to 10%, preferably about from 0.3 to 5%, and more preferably about from 0.5 to 3% in the case of a hyaluronic acid having a molecular weight of 500,000 or more, while varying according to the molecular weight of the starting hyaluronic acid.

The aqueous medium as a solvent of the photoreactive hyaluronic acid derivative solution to be irradiated with light includes water, a buffer, physiological saline, buffered physiological saline and the like. For biomedical material use, a buffer, physiological saline, and buffered physiological saline (e.g., phosphate-buffered physiological saline (PBS) and the like) are particularly preferred. When an aqueous medium other than water is used, the kind of the medium and the concentration of the solute can be used to finely control the physical properties of the resulting gel of the present invention and are selected appropriately depending on the use purpose.

The photoreactive hyaluronic acid derivative solution is usually prepared by dissolving a photoreactive hyaluronic acid derivative once separated and purified from the synthetic reaction system in an aqueous medium. As for the photoreactive hyaluronic acid derivative solution, it is possible in some cases to use a photoreactive hyaluronic acid derivative in the synthetic reaction system as it is or as its concentrated state.

When DS of the photoreactive hyaluronic acid derivative is fixed, the proportion of cyclobutane ring formation, i.e., crosslinking ratio, is apt to change with variation in the ranges of the photoreaction concentration mentioned above, and the physical properties of the resulting gel vary accordingly. With an increase in photoreaction concentration, the crosslinking ratio seems to increase, and the elasticity nature of the gel increases as verified by measurement of viscoelasticity of the photocured crosslinked-hyaluronic acid gel. With an increase in crosslinking ratio, the network structure becomes denser. The proportion of the cyclobutane ring in the photocured crosslinked-hyaluronic acid gel can be defined as a crosslinking extent which is a product of DS and a crosslinking ratio and expressed in terms of molar ratio (%) of dimers per constituent disaccharide unit of hyaluronic acid. A preferred crosslinking extent is in the ranges from 0.01 to 0.5% per mole of a constituent disaccharide unit of hyaluronic acid.

The water absorption of a dried photocured crosslinked-hyaluronic acid gel (hereinafter simply referred to a "dried gel") is influenced by the degree of crosslinking, and thus becomes a measure of the degree of the crosslinking. The water absorption is expressed by the following formula:

Water absorption (%)=Weight of absorbed water/weight of dried gel×100

As the degree of crosslinking, i.e., the crosslinking ratio, increases, the network structure becomes denser, and the uptake of water decreases, resulting in a reduced water absorption of the dried gel. The water absorption of the dried gel of the present invention is usually about from 20 (×100%) to 150 (×100%), preferably from 30 (×100%) to 120 (×100%), more preferably from 40 (×100%) to 100 (×100%), when that of the dried gel is measured after 24-hour immersion in physiological saline (0.9% sodium chloride aqueous solution) as an aqueous medium.

The gel of the present invention may be a gel containing from 0.5 to 10% by weight, in terms of hyaluronic acid content, of the photocured crosslinked-hyaluronic acid derivative. In particular, a photocured crosslinked-hyaluronic acid gel prepared from a photoreactive hyaluronic acid derivative having a weight average molecular weight of about 1,000,000 preferably has a hyaluronic acid content of from 1 to 4% by weight in the gel.

The physical properties of the gel by viscoelasticity can be expressed by dynamic viscoelastic characteristics such as storage modulus (G'), loss modulus (G"), tangent delta (tan $\delta$; G"/G') and the like. A high storage modulus and a low loss modulus indicate high elasticity, meaning a hard gel. Reversely, a high loss modulus and a low storage modulus mean a gel with high viscosity.

The gel of the present invention shows the physical properties with ranges of a storage modulus (G') of from 50 to 1500 Pa, preferably from 100 to 500 Pa; a loss modulus (G") of from 10 to 300 Pa, preferably from 50 to 150 Pa; and a tangent delta (tan $\delta$; G"/G') of from 0.1 to 0.8, preferably from 0.2 to 0.5, in dynamic viscoelasticity at a frequency of 10 Hz.

In irradiation with light, i.e., ultraviolet rays, kind of ultraviolet rays, are not particularly limited. Irradiation with light or ultraviolet rays is usually carried out for from several seconds to several minutes by using a light source providing light containing wavelengths necessary for photoreaction, i.e., from 200 to 450 nm (for example, a high pressure mercury lamp, a metal halide lamp or the like) while cutting short wavelengths undesired for dimerization with an ultraviolet rays cut filter or the like (e.g., Pyrex glass (trade name) or the like). The manner of irradiation is not particularly limited and various ones are selected appropriately according to the purpose. For example, the photoreactive hyaluronic acid derivative solution is charged in a container to be supplied as a final commercial product of the gel of the present invention and irradiated as hereinafter described; the said solution is held in between a pair of belt conveyors made of sheets of a ultraviolet ray-transmitting material and irradiated while being moved; or the photoreactive hyaluronic acid solution is fed through inside of a tube made of an ultraviolet ray-transmitting material and irradiated with ultraviolet rays while being fed.

In the process of preparation of the gel of the present invention, the gel that satisfies the above-described viscoelasticity requirements can be obtained even when the photoreactive hyaluronic acid derivative solution is subjected to a heat treatment before and/or after the irradiation with ultraviolet rays with high pressure steam of from 100 to 125° C. for from 5 to 30 minutes (autoclaving). These heat treatments can be corresponded to sterilization process required for medical devices or medicines.

The conditions of the photoreactive hyaluronic acid derivative solution to be irradiated with ultraviolet rays and the material and shape of the container for receiving it for a photoreaction and of the ultraviolet ray-receiving part are not particularly limited provided that the ultraviolet rays can be transmitted therethrough. For example, they can be layer-like, tube-like, syringe-like, vial-like or the like. Taking uniformity of crosslinking reaction into consideration, the shape should be such that ultraviolet rays transmit uniformly and sufficiently therethrough. Irradiation with ultraviolet rays to a solution layer shaped into a thin layer is particularly suitable for obtaining a uniformly crosslinked gel. The container for a photoreaction may have a shape that can hold the solution of the photoreactive hyaluronic acid derivative and the resulting gel of the present invention in a photoreaction system and does not always need to be a closed container. For example, the container may be a simple plate shape.

Where the gel of the present invention is used as a biomedical material such as an antiadhesive material, the container for preservation of the gel of the present invention preferably may have a shape with which the resulting gel of the present invention can be preserved sterilely until its use and from which the gel can be taken out properly on its use. Such a preservation container may be also used for a container for a photoreaction. Examples of such a container in which the gel can be preserved sterilely until its use and from which the gel can easily be applied to an administration object or site (when the gel is used as an antiadhesive material, the object or site is an affected part which should be protected from adhesions) include containers such as a syringe, a tube and the like. Furthermore, examples of such a container in which the gel can be easily taken out and applied include containers such as a vial and the like.

When the photoreactive hyaluronic acid derivative is charged in the container, and the charged photoreactive hyaluronic acid derivative is irradiated with ultraviolet rays to undergo photoreaction as mentioned above, the container material must be selected from such a material that transmits ultraviolet rays and undergoes no degradation by ultraviolet rays. Further, in the case where the gel of the present invention is intended to be applied to human body as a biomedical material, the gel after photoreaction may be preferably sterilized by, for example, high pressure steam (autoclaving). When the photocured crosslinked gel as charged in the container is sterilized by autoclaved sterilization, the container material may be preferably made of glass, plastics or the like having heat resistance to some extent. The amount of the gel to be charged in said container is not particularly limited; however, it is, for example, about from 0.5 to 500 ml based on the operational and economical considerations and the like.

It is possible that the hydrogel obtained by light irradiation as described above may be dehydrated by, for example, drying or the like and then swollen by addition of a desired amount of an aqueous medium to provide the gel having the above-described physical properties of the present invention. In this case, the drying is preferably performed by a method that gives no adverse influence on the hyaluronic acid saccharide chain and the crosslinked structure.

It is also possible to store or transport the photocured crosslinked-hyaluronic acid gel in the form of such a dried solid gel as mentioned above, and to use as re-swollen state with an appropriate aqueous medium immediately before use.

The gel of the present invention is of great use as a biomedical material. The high inherent biocompatibility of hyaluronic acid combined with the newly added characteristics through crosslinking such as a prolonged duration in the living body (improvement in remainability) and improved physicochemical properties such as viscoelasticity and the like suitable for use as a biomedical material make the gel of the present invention be much suited for use in the medical field.

Since the gel of the present invention comprises harmless and non-toxic aqueous medium for the most part, it does not exhibit toxicity to the living bodies and has high safety for the living bodies.

More specifically, a single dose administration of 100 ml/kg intraperitoneally (corresponding to 2000 mg of hyaluronic acid per kg) of the gel of the present invention to rats brought about no death and no serious disorder that were attributed to the gel.

Furthermore, an antigenicity test was carried out to examine active anaphylaxis, in which guinea pigs were intraperitoneally sensitized with 20 mg or 2 mg of the gel of the present invention, and then 40 mg of the gel was again intraperitoneally administered. As a result, no anaphylactic reaction was induced.

When the gel of the present invention is used as a biomedical material, e.g., an antiadhesive material, it is considered that the increased elasticity of the gel brings about improvement in barrier effect between tissues and remainability in the body, while the increased viscosity achieves improvement in stickiness to the tissue and injectability into an affected part. Therefore, it is preferably desirable for the gel for such use to have well-balanced elasticity and viscosity. If G' exceeds 1500 or the tangent delta is less than 0.1, the gel becomes highly elastic gel, so-called hard and brittle gel, and it becomes difficult for the gel to inject into an affected part. On the other hand, if G' is less than 50 or the tangent delta exceeds 0.8, the gel becomes highly viscous gel behaving like a solution, failing to provide desirable hardness, and a barrier effect required for antiadhesive effect is lost. That is, the gel of the present invention is regarded to have the most suitable physicochemical properties as an antiadhesive material.

An adhesion of organs, for example, which often occurs after operation is undesirable from the clinical standpoint, and development of an effective antiadhesive material has been desired from these standpoints. Desirable characteristics for an antiadhesive material is as follows: the material is (1) to have a barrier effect between organs which are liable to suffer an adhesion, (2) to have covering properties over a wounded part, (3) not to delay healing of a wound, (4) to be remained in the body during a healing period and preferably be degraded and absorbed within the body after healing, (5) to be harmless, non-toxic, biocompatible and the like.

The photocured crosslinked-hyaluronic acid gel of the present invention which is obtained by photocured crosslinking and has excellent biocompatibility and safety satisfies all these requirements described above. The barrier effect, which is of special importance, is secured by the physicochemical properties of the crosslinked gel, and the remainability in the body is achieved by the formation of a photocured crosslinked network structure.

The amorphousness of the gel, for example, allows the gel to be injected through an injection nozzle or needle, that is, charged into a syringe, and injected into a fine affected part (e.g., wounded part and the like). In this connection, the gel of the present invention is characterized by having far higher elasticity than that of a hyaluronic acid solution but having hardness showing such softness to pass through the needle of a syringe. The gel can also be injected to an affected part through a small-diameter tube (injection nozzle) and is expected to be applied to laparoscopic microsurgery and the like.

In brief, the antiadhesive material comprising the gel of the present invention as described above is characterized as follows:

(1) having excellent antiadhesive effect;
(2) being a hydrogel having physical properties allowing injection to an affected part;
(3) exhibiting high stickiness to tissues and also excellent stickiness to tissues when injected or applied, thereby remaining at the affected part for a period necessary for antiadhesion;

(4) having no need of removal and also being absorbable from the objective site of application such as the abdominal cavity and the like, metabolized and excreted; and (5) having safety: no problem in safety was observed in any animal tests of a single dose toxicity test, a repeated dose toxicity test and an antigenicity test.

Applicable fields when the gel of the present invention is used as an antiadhesive material are exemplified as follows.

(1) Obstetrics and Gynecology Field

Antiadhesions for adhesions accompanying intrapelvic operation for the treatment of acyesis, uterus operation, tubal operation, ovarian operation, endometriosis treatment operation, cesarean section, intrapelvic adhesiotomy or the like.

(2) Gastrointestinal Operation Field

Antiadhesions for adhesions accompanying intestine adhesion after abdominal operation or the like.

(3) Orthopedics Field

Antiadhesions for adhesions accompanying operation on Achilles tendon, operation on flexor muscles and tendons, arthroplasty, laminectomy or the like.

Applications of the gel of the present invention to the medical field as a biomedical material other than an antiadhesive material described above are shown below.

(1) Adjuvants for ophthalmologic operation. For example, the gel is injected into the anterior chamber in operations such as intraocular lens insertion, total corneal transplantation or the like, or the gel is used for maintenance of the intraocular pressure in retinal detachment and the like or for replenishment of the vitreous body.

(2) Joint function improving agents. For example, the gel is injected to articular cavity for the purpose of abatement of pain, improvement on joint mobile range, normalization of morbid synovial fluid and the like in the treatment of arthritis such as arthritis deformans in a knee joint, periarthritis in a shoulder joint or the like.

(3) Defect prostheses in plastic surgery field.

(5) Dressings for bedsores or burns.

(6) Materials or preparations for sustained release of a drug.

For the use as an antiadhesive material of the gel of the present invention, the amount of the gel to be applied to an affected part cannot be specified because it varies depending on the type (e.g., the kind of the organ and the like), size or conditions of the site of application and the purpose of application. It is usually about from 0.5 to 500 ml/site, preferably about from 1 to 100 ml/site, more preferably about from 2 to 50 ml/site.

The photocured crosslinked-hyaluronic acid gel of the present invention has a three-dimensional network structure. Incorporation of a drug into the network will provide a useful preparation for sustained release of the drug. Drug incorporation into the gel can be effected by immersing a dried gel in a solution containing a drug. Also, since the photocured crosslinked gel needs no purification after the crosslinking, a drug may previously be added to a solution of the photoreactive hyaluronic acid derivative to be irradiated. Either methods described above may be used.

Furthermore, a drug can be chemically bound to the photoreactive hyaluronic acid derivative through a chemical bonding (a covalent bonding, an ionic bonding and the like) and then may be subjected to photoreaction to be crosslinked. For example, when a drug is introduced by a covalent bonding, the drug and the carboxyl or hydroxyl group of a photoreactive hyaluronic acid derivative may be combined via an amide or ester bond, and then be subjected to irradiation with ultraviolet rays. Also, when a drug is introduced by an ionic bonding, a cationic drug capable of binding to a carboxyl group of hyaluronic acid via an ionic binding may be mixed with photoreactive hyaluronic acid, and then be subjected to irradiation with ultraviolet rays. Moreover, a photoreactive hyaluronic acid derivative containing a photoreactive crosslinking group to which a drug is linked may be subjected to photoreaction for crosslinking.

EXAMPLE

The present invention will now be illustrated in greater detail with reference to Preparation Examples, Examples, and Test Examples, but it should be understood that the present invention is not deemed to be limited thereto.

Preparation Example 1

Preparation of Photoreactive Hyaluronic Acid Derivative (DS 0.53%)

In 1.5 l of water was dissolved 10 g (25 mmol disaccharide unit) of sodium hyaluronate (a product of Seikagaku Corporation; weight average molecular weight (Mw): 950,000), and 750 ml of 1,4-dioxane was added to the solution. To the solution were added successively 50 ml of a dioxane solution containing 288 mg (2.5 mmol) of N-hydroxysuccinimide, 50 ml of an aqueous solution containing 1240 mg (1.25 mmol) of EDC.HCl, and 50 ml of an aqueous solution containing 355 mg (1.25 mmol) of $HCl.H_2N(CH_2)_6OCOCH=CHPh$ at 5-minute intervals while cooling with ice. After stirring the mixture at room temperature for 8 hours, an aqueous solution of 10 g of a sodium chloride was added thereto, followed by stirring for 1 hour. The resulting solution was poured into 5 l of ethanol. The desired precipitate thus formed was collected by centrifugation (4000 rpm×15 min), washed successively with 3 portions of 80% ethanol and a single portion of ethanol, and dried to give 9.73 g of a photoreactive hyaluronic acid derivative as a white solid (DS: 0.53%; endotoxin: 0.8 pg/mg).

The endotoxin in this Preparation Example and the following Preparation Examples and Examples was determined by using Toxicolor System LS-20 set, DIA set and Et-1 set, all available from Seikagaku Corporation (trademark; hereinafter the same).

The endotoxin content of the photocured crosslinked-hyaluronic acid gel was determined by the above-described method after the photocured crosslinked-hyaluronic acid gel described in Examples is solubilized by enzyme (e.g., chondroitinase ABC, a product of Seikagaku Corporation and the like) digestion.

In the endotoxin content, one endotoxin unit (EU) corresponds to 345 pg of endotoxin.

Preparation Example 2

Preparation of Photoreactive Hyaluronic Acid Derivative (DS 0.75%)

This was prepared in the same manner as in Preparation Example 1 using 10 g (25 mmol disaccharide unit) of sodium hyaluronate (a product of Seikagaku Corporation; Mw: 950,000), 65 ml of a 0.05 M solution of N-hydroxysuccinimide (3.25 mmol) in dioxane, 65 ml of a 0.025 M aqueous solution of EDC.HCl (1.625 mmol), and 65 ml of a 0.025 M aqueous solution of $HCl.H_2N(CH_2)_6OCOCH=CHPh$ (1.625 mmol). The obtained photoreactive hyaluronic acid derivative was 9.74 g as a white solid (DS: 0.75%; endotoxin: 2.5 pg/mg).

Preparation Example 3

Preparation of Photoreactive Hyaluronic Acid Derivative (DS 0.90%)

This was prepared in the same manner as in Preparation Example 1 using 2.0 g (5.0 mmol disaccharide unit) of sodium hyaluronate (a product of Seikagaku Corporation; Mw: 950,000), 3 ml of an aqueous solution containing 69 mg (0.6 mmol) of N-hydroxysuccinimide, 3 ml of an aqueous solution containing 58 mg (0.3 mmol) of EDC.HCl, and 3 ml of an aqueous solution containing 85 mg (0.3 mmol) of HCl.H$_2$N(CH$_2$)$_6$OCOCH=CHPh. The obtained photoreactive hyaluronic acid derivative was 2.1 g as a white solid (DS: 0.90%; endotoxin: 2.4 pg/mg).

Preparation Example 4

Preparation of Photoreactive Hyaluronic Acid Derivative (DS 1.06%)

This was prepared in the same manner as in Preparation Example 1 using 10 g (25 mmol disaccharide unit) of sodium hyaluronate (a product of Seikagaku Corporation; Mw: 950,000), 100 ml of a 0.05 M solution of N-hydroxysuccinimide (5.0 mmol) in dioxane, 100 ml of a 0.025 M aqueous solution of EDC.HCl (2.5 mmol), and 100 ml of a 0.025 M aqueous solution of HCl.H$_2$N(CH$_2$)$_6$OCOCH=CHPh (2.5 mmol). The obtained photoreactive hyaluronic acid derivative was 9.64 g as a white solid (DS: 1.06%; endotoxin: 3.2 pg/mg).

Preparation Example 5

Preparation of Photoreactive Hyaluronic Acid Derivative (DS 1.26%)

This was prepared in the same manner as in Preparation Example 1 using 5 g (12.5 mmol disaccharide unit) of sodium hyaluronate (a product of Seikagaku Corporation; Mw: 950,000), 50 ml of a solution of 288 mg (2.5 mmol) of N-hydroxy-succinimide in dioxane, 50 ml of an aqueous solution of 240 mg (1.25 mmol) of EDC.HCl, and 50 ml of an aqueous solution of 355 mg (1.25 mmol) of HCl.H$_2$N(CH$_2$)$_6$OCOCH=CHPh. The obtained photoreactive hyaluronic acid derivative was 4.9 g as a white solid (DS: 1.26%; endotoxin: 1.0 pg/mg).

Preparation Example 6

Preparation of Photoreactive Hyaluronic Acid Derivative (DS 1.29%)

This was prepared in the same manner as Preparation Example 1 using 10 g (25 mmol disaccharide unit) of sodium hyaluronate (a product of Seikagaku Corporation; Mw: 950,000), 50 ml of a 0.1 M solution of N-hydroxysuccinimide (5.0 mmol) in dioxane, 50 ml of a 0.05 M aqueous solution of EDC.HCl (2.5 mmol), and 50 ml of a 0.05 M aqueous solution of HCl.H$_2$N(CH$_2$)$_6$OCOCH=CHPh (2.5 mmol). The obtained photoreactive hyaluronic acid derivative was 10.0 g as a white solid (DS: 1.29%; endotoxin: 2.5 pg/mg).

Preparation Example 7

Preparation of Photoreactive Hyaluronic Acid Derivative (DS 1.55%)

This was prepared in the same manner as Preparation Example 1 using 10 g (25 mmol disaccharide unit) of sodium hyaluronate (a product of Seikagaku Corporation; Mw: 950,000), 150 ml of a 0.05 M solution of N-hydroxysuccinimide (7.5 mmol) in dioxane, 150 ml of a 0.025 M aqueous solution of EDC.HCl (3.75 mmol), and 150 ml of a 0.025 M aqueous solution of HCl.H$_2$N(CH$_2$)$_6$OCOCH=CHPh (3.75 mmol). The obtained photoreactive hyaluronic acid derivative was 9.92 g as a white solid (DS: 1.55%; endotoxin: 1.2 pg/mg).

Preparation Example 8

Preparation of Photoreactive Hyaluronic Acid Derivative (DS 1.93%)

In 600 ml of water was dissolved 4.0 g (10.0 mmol disaccharide unit) of sodium hyaluronate (a product of Seikagaku Corporation; Mw: 950,000), and 300 ml of 1,4-dioxane was added to the solution. To the solution were added successively 10 ml of an aqueous solution containing 230 mg (2.0 mmol) of N-hydroxysuccinimide, 10 ml of an aqueous solution containing 192 mg (1.0 mmol) of EDC.HCl, and 10 ml of an aqueous solution containing 284 mg (1.0 mmol) of HCl.H$_2$N(CH$_2$)$_6$OCOCH=CHPh at 5-minute intervals while cooling with ice. After stirring the mixture at room temperature for 24 hours, an aqueous solution of 2.0 g of a sodium chloride was added thereto, followed by stirring. The resulting solution was poured into 3.0 l of ethanol. The desired precipitate thus formed was collected by centrifugation (4000 rpm×15 min), washed successively three times with 80% ethanol and once with ethanol, and dried to give 4.1 g of a photoreactive hyaluronic acid derivative as a white solid (DS: 1.93%; endotoxin: 2.1 pg/mg).

Preparation Example 9

Preparation of Photoreactive Hyaluronic Acid Derivative (DS 2.87%)

This was prepared in the same manner as in Preparation Example 1 using 10 g (25 mmol disaccharide unit) of sodium hyaluronate (a product of Seikagaku Corporation; Mw: 950,000), 50 ml of a solution of 864 mg (7.5 mmol) of N-hydroxy-succinimide in dioxane, 50 ml of an aqueous solution of 718 mg (3.75 mmol) of EDC.HCl, and 50 ml of an aqueous solution of 1.06 g (3.75 mmol) of HCl.H$_2$N(CH$_2$)$_6$OCOCH=CHPh. The obtained photoreactive hyaluronic acid derivative was 10 g as a white solid (DS: 2.87%; endotoxin: 2.8 pg/mg).

Preparation Example 10

Preparation of Photoreactive Hyaluronic Acid Derivative (DS 2.28%)

This was prepared in the same manner as in Preparation Example 1 using 50 g (125 mmol disaccharide unit) of sodium hyaluronate (a product of Seikagaku Corporation; Mw: 950,000), 250 ml of an aqueous solution of 3.45 g (30 mmol) of N-hydroxysuccinimide, 250 ml of an aqueous solution of 2.88 g (15 mmol) of EDC.HCl, and 250 ml of an aqueous solution of 15 mmol of HCl.H$_2$N(CH$_2$)$_6$OCOCH=CHPh. The obtained photoreactive hyaluronic acid derivative was 49 g as a white solid (DS: 2.28%; endotoxin: 3.2 pg/mg).

Example 1

This Example relates to a photocured crosslinked-hyaluronic acid gel that was obtained by photocured crosslinking of the photoreactive hyaluronic acid derivative obtained in Preparation Example 6 in an aqueous solution, followed by displacement of the medium with 1.5 mM phosphate buffered physiological saline (pH 7.4).

A 1.4 wt % aqueous solution of the photoreactive hyaluronic acid derivative (DS: 1.29%) obtained in Preparation Example 6 was held between a pair of Pyrex glass plates each having a thickness of 2.5 mm spaced at 1.0 mm, irradiated with ultraviolet rays (3 KW metal halide lamp) for 4 minutes from each side (8 minutes in total), and then dried at 45° C. To the resulting dried gel was added 1.5 mM phosphate buffered physiological saline (pH 7.4) adjusting a concentration to 2 wt %. Then the dried gel was swollen for 1 day to obtain a photocured crosslinked-hyaluronic acid gel (endotoxin: 0.11 EU/g).

Example 2

This Example relates to photocured crosslinked-hyaluronic acid gels that were obtained by photocured crosslinking of the photoreactive hyaluronic acid derivatives obtained in Preparation Examples 1, 4, and 7 in a 1.4 wt % solution in 1.5 mM phosphate buffered physiological saline (pH 7.4).

A 1.4 wt % solution of each of the photoreactive hyaluronic acid derivatives obtained in Preparation Examples 1, 4, and 7 (DS: 0.53%, 1.06% and 1.55%, respectively) in 1.5 mM phosphate buffered physiological saline (pH 7.4) was held between a pair of Pyrex glass plates each having a thickness of 2.5 mm spaced at 1.0 mm, irradiated with ultraviolet rays (3 KW metal halide lamp) for 4 minutes from each side (8 minutes in total) to obtain a photocured crosslinked-hyaluronic acid gel.

The endotoxin content was 0.03, 0.12 and 0.05 EU/g in the gels having DS of 0.53%, 1.06% and 1.55%, respectively.

Example 3

This Example relates to photocured crosslinked-hyaluronic acid gels that were obtained by photocured crosslinking of the photoreactive hyaluronic acid derivatives obtained in Preparation Examples 1 to 9 in a 2.0 wt % solution in 1.5 mM phosphate buffered physiological saline (pH 7.4).

A 2.0 wt % solution of each of the photoreactive hyaluronic acid derivatives obtained in Preparation Examples 1 to 9 (DS: 0.53%, 0.75%, 0.90%, 1.06%, 1.26%, 1.29%, 1.55%, 1.93%, and 2.87%, respectively) in 1.5 mM phosphate buffered physiological saline (pH 7.4) was held between a pair of Pyrex glass plates each having a thickness of 2.5 mm spaced at 1.0 mm, irradiated with ultraviolet rays (3 KW metal halide lamp) for 4 minutes from each side (8 minutes in total) to obtain a photocured crosslinked-hyaluronic acid gel.

Example 4

This Example relates to photocured crosslinked-hyaluronic acid gels that were obtained by photocured crosslinking of the photoreactive hyaluronic acid derivatives obtained in Preparation Examples 1, 4, and 7 in a 3.2 wt % solution in 1.5 mM phosphate buffered physiological saline (pH 7.4).

A 3.2 wt % solution of each of the photoreactive hyaluronic acid derivatives obtained in Preparation Examples 1, 4, and 7 (DS: 0.53%, 1.06%, and 1.55%, respectively) in 1.5 mM phosphate buffered physiological saline (pH 7.4) was held between a pair of Pyrex glass plates each having a thickness of 2.5 mm spaced at 1.0 mm, irradiated with ultraviolet rays (3 KW metal halide lamp) for 4 minutes from each side (8 minutes in total) to obtain a photocured crosslinked-hyaluronic acid gel.

Example 5

This Example relates to photocured crosslinked-hyaluronic acid gels that were obtained by heat treatment of the photocured crosslinked-hyaluronic acid gels having DS of 1.55% and 2.87% in Example 3.

The photocured crosslinked-hyaluronic acid gels obtained in Example 3 from the photoreactive hyaluronic acid derivatives having DS of 1.55% and 2.87% were each charged in a 10 ml ampule and subjected to heat treatment by autoclaving at 121° C. for 8 minutes.

Measurement of Physical Properties

The dynamic viscoelasticity (storage modulus G', loss modulus G", tangent delta tan δ (G"/G')), dynamic viscosity (η) and water absorption of solutions of the photoreactive hyaluronic acid derivatives obtained in Preparation Examples 1, 4, 5 and 7 having a preparation concentration (solution concentration: as hyaluronic acid concentration) of 1.4 wt %, 2.0 wt % or 3.2 wt %, the photocured crosslinked-hyaluronic acid gels prepared in Examples 2 to 4 having a preparation concentration of 1.4 wt %, 2.0 wt % or 3.2 wt % and the heat-treated photocured crosslinked-hyaluronic acid gels prepared in Example 5 were measured. The physical properties of hyaluronic acid solution prepared so that the preparation concentration became the same as that of the above-mentioned photocured crosslinked-hyaluronic acid gel were measured as described above. The measurement of the dynamic viscoelasticity and dynamic viscosity was made with a rheometer Model CSL-50 manufactured by Carri-Med under the following conditions.

Method of measurement: oscillation test method, stress control

Measuring temperature: 37° C.

Measuring geometry: 4 cm

Gap: 800 μm

Frequency: 10 Hz

The water absorption was calculated by an ultraviolet absorbance method using Blue Dextran (hereinafter abbreviated as "B.D.") disclosed in EP 0205674 A1 as follows. Physiological saline (0.9% sodium chloride aqueous solution) was used as an aqueous medium.

When a dried gel is put in a B.D. solution, the gel absorbs only water because B.D. having a high molecular weight cannot enter the gel. Correspondingly, the concentration of the B.D. solution remaining unabsorbed is increased over the initial one depending on water absorbed. This difference in concentration is obtained from absorbances (610 nm), and the water absorption can then be calculated according to equation:

$$\text{Water absorption } (\times 100\%) = (1 - y1/y2)/A \times 1000$$

wherein y1 is the absorbance at the initial concentration of A mg of a dried gel per gram of a 0.1 wt % B.D. solution; and y2 is the absorbance after 24-hour swelling in the B.D. solution.

Further, the water absorption was examined on the dried samples of the photocured crosslinked-hyaluronic acid gels prepared in Example 3 from the photoreactive hyaluronic acid derivatives having DS of 0.53%, 0.75%, 0.90%, 1.26%, 1.55% and 1.93%.

Figure 2:
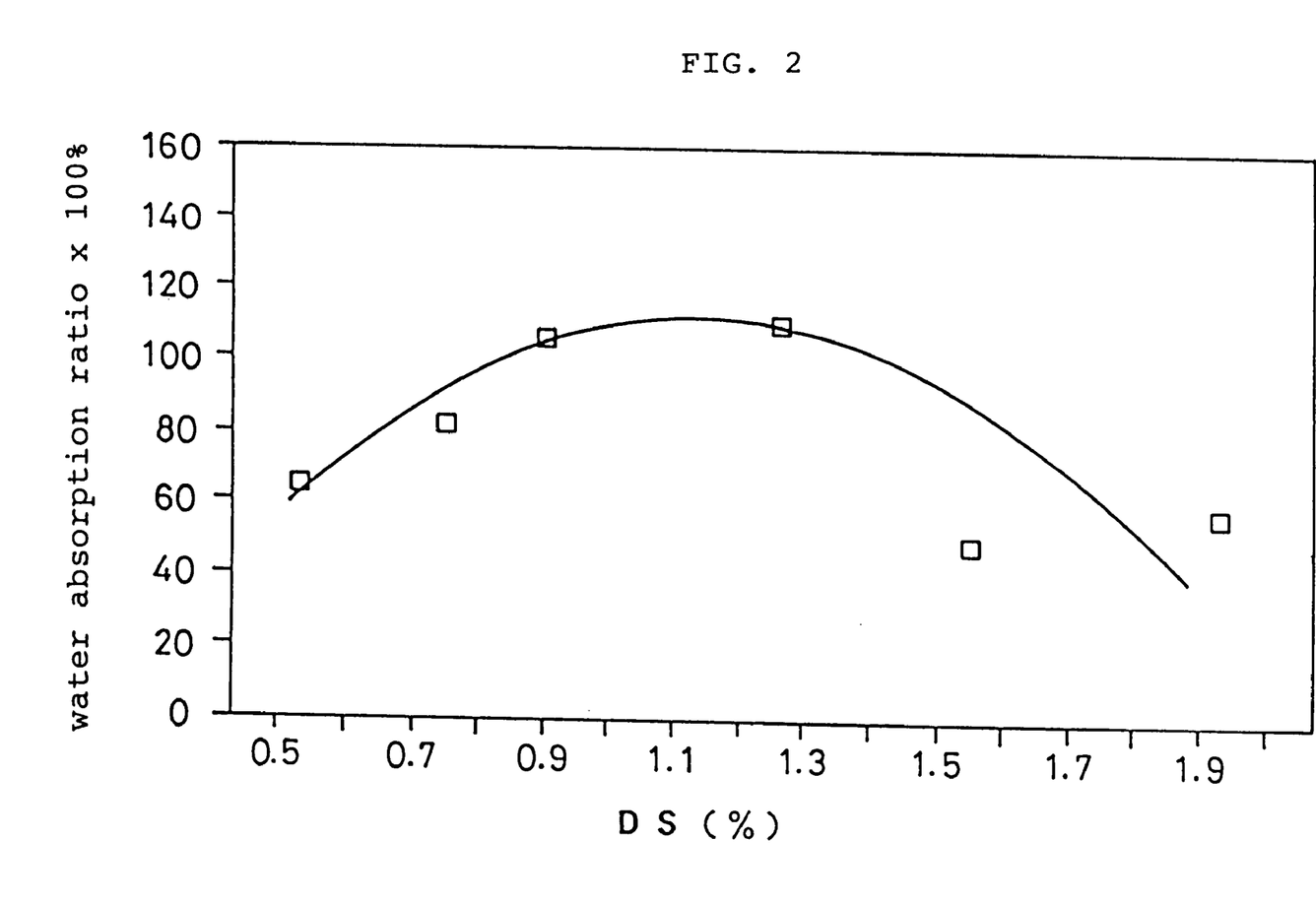
FIG. 2 is a graph showing the relationship between DS (degree of substitution) and water absorption ratio of a photocured crosslinked-hyaluronic acid gel.

Some of the results of the measurement of dynamic viscoelasticity and the like are shown in Table 1, and the relationship between DS and water absorption is shown in FIG. 2. In Table 1, the found concentrations of the samples under analysis were obtained by determining the hyaluronic acid component content of the gel according to a carbazole-sulfuric acid reaction method.

TABLE 1

| Example No. | DS (%) | Concentration (prepared) (%) | Concentration (found) (%) | Heat Treatment | Frequency: 10 Hz | | | |
|---|---|---|---|---|---|---|---|---|
| | | | | | G' (Pa) | G" (Pa) | tanδ | η (Pa · s) |
| 2 | 0.53 | 1.4 | 1.22 | — | 66 | 41 | 0.63 | 0.7 |
| | 1.06 | 1.4 | 1.37 | — | 146 | 65 | 0.45 | 1.0 |
| | 1.55 | 1.4 | 1.24 | — | 149 | 64 | 0.43 | 1.0 |
| Hyaluronic acid | | 1.4 | 1.38 | — | 46 | 44 | 0.97 | 0.7 |
| 3 | 0.53 | 2.0 | 1.96 | — | 146 | 78 | 0.53 | 1.2 |
| | 1.06 | 2.0 | 1.81 | — | 339 | 109 | 0.32 | 1.7 |
| | 1.26 | 2.0 | 1.70 | — | 273 | 96 | 0.35 | 1.5 |
| | 1.55 | 2.0 | 2.04 | — | 342 | 105 | 0.31 | 1.7 |
| | 2.87 | 2.0 | 1.62 | — | 427 | 103 | 0.24 | 1.7 |
| Hyaluronic acid | | 2.0 | 2.00 | — | 241 | 102 | 0.42 | 1.6 |
| 4 | 0.53 | 3.2 | 2.63 | — | 550 | 216 | 0.39 | 3.4 |
| | 1.06 | 3.2 | 2.77 | — | 818 | 223 | 0.27 | 3.5 |
| | 1.55 | 3.2 | 2.78 | — | 1002 | 248 | 0.25 | 3.9 |
| Hyaluronic acid | | 3.2 | 3.35 | — | 560 | 304 | 0.54 | 4.8 |
| 5 | 1.55 | 2.0 | 2.04 | 121° C., 8 min | 173 | 86 | 0.50 | 1.4 |
| | 2.87 | 2.0 | 1.62 | 121° C., 8 min | 310 | 101 | 0.32 | 1.6 |
| Hyaluronic acid | | 3.2 | 3.02 | 121° C., 8 min | 407 | 281 | 0.69 | 4.5 |

Example 6

This Example relates to photocured crosslinked-hyaluronic acid gels that were obtained by irradiation with ultraviolet rays under different conditions and heat treatment of a 2.0 wt % solution of each of the photoreactive hyaluronic acid derivative obtained in Preparation Example 10 in 1.5 mM phosphate buffered physiological saline (pH 7.4).

The photoreactive hyaluronic acid derivative having DS of 2.28% which was prepared in Preparation Example 10 was dissolved in 1.5 mM phosphate buffered physiological saline (pH 7.4) in a 2.0 wt % solution. The resulting solution was irradiated with ultraviolet rays in accordance with the following three methods. Before and/or after the irradiation with ultraviolet rays, the solution (or gel) was subjected to a heat treatment under the following conditions. The crosslinking ratio, crosslinking extent, and viscoelasticity characteristics of the resulting gels were measured.

Conditions of Irradiation with Ultraviolet Rays (UV Irradiation)

(1) The same method as in Examples 2 to 4. The aqueous solution of the photoreactive hyaluronic acid derivatives was held between a pair of Pyrex glass plates each having a thickness of 2.5 mm spaced at 1.0 mm and irradiated with ultraviolet rays of a 3 KW metal halide lamp for 4 minutes from each side (8 minutes in total).
(2) The solution was held between a pair of polyethylene films and irradiated with ultraviolet rays of a 400 W high pressure mercury lamp for 3 seconds from one side.
(3) The solution was irradiated using a 400 W high pressure mercury lamp while being fed through a quartz-made tube with 5 mm in diameter.

Conditions of Heat Treatment (Autoclaving Method)
A: After UV irradiation; 121° C., 8 min
B: Before UV irradiation; 121° C., 8 min
C: Before UV irradiation; 121° C., 8 min and then after UV irradiation; 100° C., 10 min
D: After UV irradiation; 121° C., 15 min The results of the measurements are shown in Table 2 below.

Wherein the crosslinking ratio was calculated from the following equation.

Crosslinking ratio (%)=Number of moles of dimerized cinnamic acid×2/number of moles of introduced cinnamic acid×100

More specifically, cinnamic acid or its dimer was chemically cleaved and extracted from a photocured crosslinked-hyaluronic acid gel. Taking advantage of the difference in molecular weight between cinnamic acid and its dimer, the extract was separated into cinnamic acid and its dimer by gel-permeation chromatography (GPC), and each component was quantitatively determined to obtain the respective number of moles. Then, the crosslinking ratio was calculated based on the above equation.

The crosslinking extent was obtained from the following equation.

Crosslinking extent (%)=DS×Crosslinking ratio/100

As is seen from the above equations, while the crosslinking ratio is a value based on the introduced cinnamic acid, the crosslinking extent (the product of the crosslinking ratio and DS) can be expressed as a molar ratio (%) of dimers per constituent disaccharide unit of hyaluronic acid.

TABLE 2

| DS (%) | Condition of Light Irradiation | Condition of Heat Treatment | Ratio of Cross-linking (%) | Extent of Crosslinking (%) | Frequency: 10 Hz | | | |
|---|---|---|---|---|---|---|---|---|
| | | | | | G' (Pa) | G" (Pa) | tanδ | η (Pa · s) |
| 2.28 | (1) | A | 4.1 | 9.4 × 10$^{-2}$ | 161 | 68 | 0.42 | 1.1 |
| 2.28 | (2) | A | 1.9 | 4.4 × 10$^{-2}$ | 122 | 68 | 0.46 | 0.9 |

TABLE 2-continued

| DS (%) | Condition of Light Irradiation | Condition of Heat Treatment | Ratio of Cross-linking (%) | Extent of Crosslinking (%) | Frequency: 10 Hz G' (Pa) | G" (Pa) | tanδ | η (Pa · s) |
|---|---|---|---|---|---|---|---|---|
| 2.28 | (3) | B | 2.5 | $5.6 \times 10^{-2}$ | 146 | 68 | 0.48 | 1.1 |
| 2.28 | (3) | C | 2.5 | $5.6 \times 10^{-2}$ | 144 | 68 | 0.59 | 1.3 |
| 2.28 | (2) | D | 1.9 | $4.4 \times 10^{-2}$ | 108 | 68 | 0.78 | 1.3 |

Test Example 1

Antiadhesion Effect in Rat Uterine Horn Model

This Test Example relates to the antiadhesion effect of the gels obtained in Examples 1, 3, 5 and 6 and, for comparison, the photoreactive hyaluronic acid derivative solutions before irradiation with ultraviolet rays as prepared in Examples 1 and 3 (hereinafter referred to as "uncrosslinked-hyaluronic acid gel"), a commercially available antiadhesive material TC7 (Interceed (trade name), produced by Johnson & Johnson), and a 3.2 wt % solution of hyaluronic acid in 1.5 mM phosphate buffered physiological saline in a rat uterine horn adhesion model.

1. Test Animal

Seven-week-old Crj:SD (SPF.) female rats were purchased and fed for 1 week before testing. Each group consisted of 5 rats.

2. Test Method 2-1. Preparation of Rat Uterine Horn Adhesion Model

The abdomen of the rat was shaved under anesthesia with Nembutal. A mid-line incision of approximately 4 cm in length was made.

(a) The right abdominal wall was cut out to the muscular layer with a trephine for ophthalmological surgery, and the muscular layer were stripped with forceps.

(b) The uterine horn was exposed, and 4 transverse incisions were made from about 1 cm down the ovary toward the cervix at 2 to 3 mm intervals. Hemostasis was carried out at any time for each cut by electric cauterization.

(c) The site about 3 to 4 mm from the end of the transverse incisions on the uterine horn and the site 3 to 4 mm from the end of the defect in the abdominal wall were put together with a single 8/0 suture to make the traumas made in (a) and (b) above close.

2-2. Administration

Test Group

Each 1 ml of the photocured crosslinked-hyaluronic acid gels, uncrosslinked-hyaluronic acid gels and the hyaluronic acid solution described above and the commercially available TC7 having an area of 1.5×1.5 cm² were injected or inserted between the defect part in the abdominal wall and the incision part of the uterine horn. More specifically, the above gels were administered as follows. Each 1 ml gel described above that was weighed accurately was taken in a 1 ml syringe (Terumo Syringe (trade name) for tuberculin; γ-ray-sterilized, inner diameter of the tube: about 4 mm; inner diameter of the tip: about 1 mm) and injected through the tip of the syringe between the defect part in the abdominal wall and the incision part in the uterine horn.

Control Group

The same operation was performed on the abdominal wall and the uterine horn on the left side of the same animal as that used for test group without insertion of materials.

3. Evaluation

Seven days after the implantation, the rats were sacrificed by exsanguination through the carotid artery under anesthesia with ethyl ether. After dissection, the site suffering an adhesion was evaluated in terms of the degree of adhesion according to the following scoring system.

0 . . . No adhesion.
1 . . . A slight and easily detachable adhesion.
2 . . . A medium and detachable adhesion.
3 . . . A serious and undetachable adhesion.

4. Results

The results of the test are shown in Table 3 below. In Table 3, the conditions of irradiation with ultraviolet rays and the conditions of heat treatment are the same as those described in Example 6.

TABLE 3

| Example No. | DS (%) | Condition of Light Irradiation | Condition of Heat Treatment | Antiadhesion Effect Test Group | Control Group |
|---|---|---|---|---|---|
| 1 | 1.29 | (1) | — | 0, 0, 0, 0, 0 | 2, 2, 2, 2, 2 |
| — | 1.29 | non-irradiated | — | 2, 2, 2, 2, 2 | 2, 2, 2, 2, 2 |
| 3 | 1.06 | (1) | — | 1, 1, 0, 0, 0 | 2, 2, 2, 2, 2 |
| 3 | 1.26 | (1) | — | 2, 0, 0, 0, 0 | 2, 2, 2, 2, 2 |
| — | 1.26 | non-irradiated | — | 2, 2, 2, 2, 0 | 2, 2, 2, 2, 2 |
| 3 | 1.55 | (1) | — | 0, 0, 0, 0, 0 | 2, 2, 2, 2, 2 |
| 5 | 1.55 | (1) | A | 0, 0, 0, 0, 0 | 2, 2, 2, 2, 2 |
| 3 | 2.87 | (1) | — | 0, 0, 0, 0, 0 | 2, 2, 2, 2, 2 |
| 5 | 2.87 | (1) | A | 0, 0, 0, 0, 0 | 2, 2, 2, 2, 2 |
| 6 | 2.28 | (2) | A | 1, 0, 0, 0, 0 | 2, 2, 2, 2, 2 |
| 6 | 2.28 | (3) | D | 1, 0, 1, 0, 0 | 2, 2, 2, 2, 2 |
| Comparison: TC7 | — | — | — | 2, 2, 2, 2, 2 | 2, 2, 2, 2, 2 |
| 3.2% Hyaluronic acid solution | — | — | A | 2, 2, 2, 2, 2 | 2, 2, 2, 2, 2 |

As can be seen from the results in Table 3, while the commercially available antiadhesive film TC7 was not entirely effective in this adhesion model, the photocured crosslinked-hyaluronic acid gel according to the present invention was proved to be sufficiently effective on antiadhesions in this model.

From the fact that no effect is drawn from the uncrosslinked gels or the 3.2% hyaluronic acid solution which had similar viscoelasticity and viscosity to those of the photocrosslinked gels, it may be thought that the antiadhesive effect of the photocured crosslinked-hyaluronic acid gel of the present invention is manifested on photocured crosslinking.

Test Example 2

This Test Example relates to the antiadhesive effect of the gel of the present invention in the same rat uterine horn adhesion model as in Test Example 1 without hemostasis for the defect part of the abdominal wall and the incision part of the uterine horn.

The antiadhesive effect of the gel of the present invention was examined and evaluated in the same manner as in Test Example 1, except for carrying out no hemostasis for the cuts of the abdominal wall and the uterine horn and using 0.5 ml of a photocured crosslinked-hyaluronic acid gel having a concentration of 2% and DS of 2.5% and having been subjected to a heat treatment at 105° C. for 10 minutes before irradiation with ultraviolet rays and at 121° C. for 8 minutes after irradiation with ultraviolet rays (n=10). As the control, the same animal as that used for test group was examined without insertion of materials in the same manner as in Test Example 1.

The results obtained are shown in Table 4.

TABLE 4

| Animal No. | Control Group | Test Group |
|---|---|---|
| 1 | 2 | 0 |
| 2 | 2 | 0 |
| 3 | 2 | 0 |
| 4 | 2 | 0 |
| 5 | 2 | 0 |
| 6 | 2 | 0 |
| 7 | 2 | 0 |
| 8 | 2 | 2 |
| 9 | 2 | 0 |
| 10 | 2 | 0 |

The photocured crosslinked-hyaluronic acid gel at a dose of 0.5 ml showed a significant effect of antiadhesion on the model receiving no hemostasis. In other words, the results in Table 4 prove the superiority of the photocured crosslinked-hyaluronic acid gel to the commercially available TC7 that cannot be applied to the affected part without carrying out hemostasis.

Test Example 3

Antiadhesion Effect of the Photocured Crosslinked-hyaluronic Acid Gel in Rat Intestinal Adhesion Model 1. Test Substance Photocured crosslinked-hyaluronic acid gel having a concentration of 2% and DS of 2.5%; heat treated at 105° C. for 10 minutes before irradiation with ultraviolet rays and at 121° C. for 8 minutes after irradiation ultraviolet rays.

2. Test Animal

Seven-week-old SD female rats were purchased and fed for 1 week before testing.

3. Preparation of Adhesion Model

The serous membrane from the ileum to the colon was peeled off linearly in a length of 20 cm and in a width of 3 to 4 mm. Hemostasis was not carried out.

4. Administration and Grouping

A prescribed amount (0.5 ml, 1.0 ml or 2.0 ml) of the gel was injected from a 1 ml syringe and applied to the affected site. After the application, the intestinal canal was returned into the abdominal cavity, and the abdomen was closed. The adhesion model without application of the gel was taken as the control group. The models applied with 0.5 ml, 1.0 ml and 2.0 ml gels were taken as 0.5 ml, 1.0 ml and 2.0 ml groups, respectively. Each group consisted of 10 rats.

5. Evaluation and Results

Seven days after the implantation, the rats were sacrificed by exsanguination through the carotid artery under anesthesia with ethyl ether. After dissection, the degree of adhesion was evaluated according to the same scoring system as in Test Example 1. The results obtained are shown in Table 5 below.

TABLE 5

| Animal No. | Control Group | Test Group | | |
|---|---|---|---|---|
| | | 0.5 ml | 10 ml | 2.0 ml |
| 1 | 2 | 0 | 0 | 0 |
| 2 | 2 | 0 | 0 | 0 |
| 3 | 2 | 1 | 0 | 0 |
| 4 | 2 | 0 | 0 | 0 |
| 5 | 2 | 0 | 0 | 0 |
| 6 | 2 | 0 | 0 | 1 |
| 7 | 2 | 0 | 0 | 0 |
| 8 | 1–2 | 0 | 0 | 0 |
| 9 | 1–2 | 1–2 | 0 | 0 |
| 10 | 1–2 | 0 | 0 | 0 |

All the three test groups showed significant antiadhesion effects compared with those of the control group. The results in Table 5 show not only the effectiveness of the gels of the present invention on antiadhesion but their superiority in tissue-stickiness and tissue-biocompatibility considering vigorous peristaltic movement of the intestine.

Furthermore, at seven days dissection after the implantation in animal tests in Test Examples 1 and 2 above, most of the administered photocured crosslinked-hyaluronic acid gel was disappeared by the naked eye. Thus biodegradability of the gel of the present invention was shown.

As described and demonstrated above, a photocured crosslinked-hyaluronic acid gal can be easily prepared by irradiation with ultraviolet rays of a high concentration aqueous solution of a photoreactive hyaluronic acid derivative. The photocured crosslinked-hyaluronic acid gel of the present invention possesses physical properties such as suitable viscoelasticity, tissue-affinity, biodegradability and the like while retaining excellently inherent properties of hyaluronic acid such as non-toxicity, non-antigenicity, biocompatibility, biodegradability and the like. Therefore, it is expected to be applied to various fields as a medical material of high safety, for example, as an antiadhesive material, a carrier for sustained release of a drug or the like. Furthermore, the gel can be injectable into fine parts of the affected sites of the body by means of a syringe, a tube or the like, and is therefore expected to be applicable to microsurgery and the like.

We claim:

1. An injectable photocured crosslinked-hyaluronic acid hydrogel having a network structure containing an aqueous medium, said gel having a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,     method of measurement:
        oscillation test method, stress control
    measuring temperature: 37° C.
    measuring geometry: 4 cm
    gap: 800 $\mu$m
    frequency: 10 Hz, and
    which is a hydrogel obtained by irradiation with ultraviolet rays of a photoreactive hyaluronic acid derivative in which a photoreactive crosslinking group is chemically linked to a functional group of the hyaluronic acid and crosslinking of mutual photoreactive crosslinking groups.
    wherein said photoreactive crosslinking group is a cinnamic acid derivative containing a spacer and chemically links to a functional group of hyaluronic acid to afford said photoreactive hyaluronic acid derivative and said mutual photoreactive crosslinking groups of said photoreactive hyaluronic acid derivative are dimerized by irradiation with ultraviolet rays to form a cyclobutane ring and to thereby form said network structure.

2. The photocured crosslinked-hyaluronic acid-hydrogel according to claim 1, which has a crosslinking extent of form 0.01 to 0.05% per mole of a constituent disaccharide unit of hyaluronic acid.

3. A photocured crosslinked-hyaluronic acid-hydrogel according to claim 1, which has a water absorption of 2,000 to 15,000% as defined as follows:

water absorption (%)=weight of absorbed water /weight of dried gel×100.

4. The photocured crosslinked-hyaluronic acid hydrogel according to claim 1, wherein said spacer is a group derived from an amino alcohol, an amino acid or a peptide.

5. The photocured crosslinked-hyaluronic acid hydrogel according to claim 1, wherein said photoreactive crosslinking group is represented by the following formula (1) or (2):

$$-\text{NH}(CR^1R^2)_n\text{OCOCH}=\text{CH}-\text{Ph} \quad (1)$$

wherein $R^1$ and $R^2$ each independently represents a hydrogen atom or an alkyl group having from 1 to 8 carbon atoms; Ph represents a phenyl group; and n represents an integer of from 2 to 18;

$$-A-\text{NH}-\text{Ph}-\text{CH}=\text{CHCOOR}^3 \quad (2)$$

wherein $R^3$ represents an alkyl group having from 1 to 8 carbon atoms or an aralkyl group; A represents $-(\text{NHCR}^4R^5\text{CO})_m-$ or $-\text{NH}(CR^4R^5)_h\text{CO}-$; $R^4$ and $R^5$ each independently represents a hydrogen atom or an alkyl group having from 1 to 8 carbon atoms; —Ph— represents a para-phenylene group; m represents an integer of from 1 to 6; and h represents an integer of from 1 to 18.

6. The photocured crosslinked-hyaluronic acid hydrogel according to claim 1, wherein said photoreactive crosslinking group is introduced in a proportion of from 0.05 to 10% per mole of a constituent disaccharide unit.

7. A photocured crosslinked-hyaluronic acid hydrogel, which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a hydrogel obtained by irradiation with ultraviolet rays of a photoreactive hyaluronic acid derivative in an aqueous medium solution in which a photoreactive crosslinking group is chemically linked to a functional group of the hyaluronic acid and crosslinking of mutual photoreactive crosslinking groups and then by a heat treatment of the crosslinked product.

8. A photocured crosslinked-hyaluronic acid hydrogel, which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a hydrogel obtained by a heat treatment of a photoreactive hyaluronic acid derivative in which a photoreactive crosslinking group is chemically linked to a functional group of the hyaluronic acid, and then by irradiation with the ultraviolet rays of the heated photoreactive hyaluronic acid derivative in an aqueous medium solution and crosslinking of mutual photoreactive crosslinking groups.

9. A photocured crosslinked-hyaluronic acid hydrogel, which has a storage modulus (G') of from 50 to 1500 Pa, a loss modulus (G") of from 10 to 300 Pa, and a tangent delta (G"/G') of from 0.1 to 0.8 in dynamic viscoelasticity measured by a rheometer under the following conditions,
method of measurement:
oscillation test method, stress control
measuring temperature: 37° C.
measuring geometry: 4 cm
gap: 800 μm
frequency: 10 Hz, and
which is a hydrogel obtained by a heat treatment of a photoreactive hyaluronic acid derivative in which a photoreactive crosslinking group is chemically linked to a functional group of the hyaluronic acid, and then by irradiation with ultraviolet rays of the heated photoreactive hyaluronic acid derivative and crosslinking of mutual photoreactive crosslinking groups, and then by a heat treatment of the crosslinked product again.

10. The photocured crosslinked-hyaluronic acid gel according to claims 1, 7, 8 and 9, wherein the endotoxin content of the gel is 0.25 endotoxin unit (EU)/g or less.

11. A method for preparing a photocured crosslinked-hyaluronic acid hydrogel comprising:
irradiating with ultraviolet rays an aqueous medium solution containing from 0.5 to 10% by weight photoreactive hyaluronic acid derivative in which a photoreactive crosslinking group is chemically linked to a functional group of the hyaluronic acid; and
forming an intermolecular and/or intramolecular crosslinking by dimerization of the mutual photoreactive crosslinking groups to provide a network structure.

12. The method for preparing a photocured crosslinked-hyaluronic acid hydrogel according to claim 11, wherein a heat treatment is conducted before and/or after irradiation with ultraviolet rays of said aqueous medium solution of the photoreactive hyaluronic acid derivative.

13. A method for preparing a photocured crosslinked-hyaluronic acid hydrogel comprising:
irradiating with ultraviolet rays an aqueous medium solution containing from 0.5 to 10% by weight photoreactive hyaluronic acid derivative in which a photoreactive crosslinking group is chemically linked to a functional group of the hyaluronic acid; and
forming an intermolecular and/or intramolecular crosslinking by dimerization of the mutual photoreactive crosslinking groups to provide a network structure,
wherein a heat treatment is conducted at from 100 to 125° C. for from 5 to 30 minutes with high pressure steam before and/or after irradiation with ultraviolet rays of said aqueous medium solution of the photoreactive hyaluronic acid derivative.

14. A biomedical material comprising the photocured crosslinked-hyaluronic acid hydrogel according to any one of claims 1, 7, 8 and 9.

15. The biomedical material according to claim 14, which has an antiadhesive effect.

16. A biomedical material kit comprising the photocured crosslinked-hyaluronic acid hydrogel as described in any one of claims 1, 7, 8 and 9, and a container containing said hydrogel in such a state that it can be taken out.

17. The biomedical material kit according to claim 16, wherein said container which can push out said hydrogel for injection.

18. The photocured crosslinking-hyaluronic acid hydrogel according to any one of claims 1, 7, 8 and 9, which is capable of being pushed out from a container.

19. The method for preparing a photocured crosslinked-hyaluronic acid hydrogel according to claim 7 or 8, wherein said heat treatment is conducted at from 100 to 125° C. for from 5 to 30 minutes with high pressure stream.

* * * * *